US012733869B2

(12) United States Patent
Park et al.

(10) Patent No.: US 12,733,869 B2
(45) Date of Patent: Sep. 15, 2026

(54) WEARABLE PRESSURE ULCER DETECTION SENSOR AND PRESSURE ULCER DETECTION SYSTEM INCLUDING THE SAME

(71) Applicant: ASEN COMPANY, Seoul (KR)

(72) Inventors: Jin-Woo Park, Seoul (KR); Seung-Rok Kim, Seoul (KR); Hye-Jun Kil, Seoul (KR); Jin-Hoon Kim, Seoul (KR); Soyeon Lee, Seoul (KR); Ju-Hyun Yoo, Seoul (KR); Je-Heon Oh, Seoul (KR); Ey-In Lee, Seoul (KR)

(73) Assignee: ASEN COMPANY, Seoul (KR)

( * ) Notice: Subject to any disclaimer, the term of this patent is extended or adjusted under 35 U.S.C. 154(b) by 133 days.

(21) Appl. No.: 18/552,422

(22) PCT Filed: Dec. 20, 2021

(86) PCT No.: PCT/KR2021/019385

§ 371 (c)(1),
(2) Date: Sep. 25, 2023

(87) PCT Pub. No.: WO2022/203164

PCT Pub. Date: Sep. 29, 2022

(65) Prior Publication Data

US 2024/0130670 A1 Apr. 25, 2024
US 2024/0225530 A9 Jul. 11, 2024

(30) Foreign Application Priority Data

Mar. 25, 2021 (KR) ........................ 10-2021-0038530

(51) Int. Cl.

*A61B 5/00* (2006.01)
*A61B 5/01* (2006.01)
*A61B 5/0531* (2021.01)

(52) U.S. Cl.

CPC ............ *A61B 5/447* (2013.01); *A61B 5/0002* (2013.01); *A61B 5/01* (2013.01); *A61B 5/0531* (2013.01);

(Continued)

(58) Field of Classification Search

CPC ......... A61B 5/447; A61B 5/01; A61B 5/0531; A61B 2562/0247; A61B 2562/0285

See application file for complete search history.

(56) References Cited

U.S. PATENT DOCUMENTS 9,664,717 B2 * 5/2017 Choi ........................ G01R 3/00
2008/0278336 A1 * 11/2008 Ortega .................. A61B 5/002 340/573.5

(Continued)

FOREIGN PATENT DOCUMENTS

CN 109069712 A 12/2018
JP 2017-527507 A 9/2017

(Continued)

OTHER PUBLICATIONS

News & Information for Chemical Engineers, vol. 36, No. 4, 2018, pp. 450-454.

(Continued)

*Primary Examiner* — Catherine M Voorhees
(74) *Attorney, Agent, or Firm* — ALSTON & BIRD LLP

(57) ABSTRACT

The present invention relates to a wearable pressure ulcer detection sensor, and the wearable pressure ulcer detection sensor according to the present invention includes a pressure sensor measuring pressure based on a change in capacitance caused by physical force, a temperature sensor measuring temperature based on a change in electrical conductivity due to electron hopping, and an impedance sensor including two electrodes spaced apart from each other and in contact with skin.

9 Claims, 2 Drawing Sheets

(52) U.S. Cl.
CPC .... *A61B 5/6804* (2013.01); *A61B 2562/0247* (2013.01); *A61B 2562/0271* (2013.01)

(56) References Cited

U.S. PATENT DOCUMENTS

| | | | | |
|---|---|---|---|---|
| 2012/0177934 | A1* | 7/2012 | Vogel | H01M 4/13 977/734 |
| 2014/0266736 | A1* | 9/2014 | Cretu-Petra | A61B 5/6808 340/573.5 |
| 2015/0177079 | A1* | 6/2015 | Eichhorn | G01L 9/0054 977/956 |
| 2016/0011063 | A1* | 1/2016 | Zhang | A61B 5/11 600/301 |
| 2017/0055851 | A1* | 3/2017 | Al-Ali | G01K 1/16 |
| 2018/0182491 | A1 | 6/2018 | Belliveau et al. | |
| 2019/0104982 | A1* | 4/2019 | Dunn | A61B 5/7264 |
| 2020/0357519 | A1 | 11/2020 | Chakravarthy et al. | |
| 2021/0127975 | A1* | 5/2021 | Rogers | A61B 5/0205 |

FOREIGN PATENT DOCUMENTS

| | | | |
|---|---|---|---|
| JP | 2018-042686 | A | 3/2018 |
| JP | 2019-217043 | A | 12/2019 |
| JP | 2020-516324 | A | 6/2020 |
| KR | 10-2018-0044942 | | 5/2018 |
| KR | 10-2018-0044942 | A | 5/2018 |
| KR | 10-2019-0111552 | | 10/2019 |
| KR | 10-2019-0111552 | A | 10/2019 |
| KR | 10-2001512 | | 10/2019 |
| KR | 10-2001512 | B1 | 10/2019 |
| KR | 10-2056006 | | 12/2019 |
| KR | 10-2056006 | B1 | 12/2019 |
| KR | 10-2020-0048938 | A | 5/2020 |
| KR | 20200048938 | | 5/2020 |
| KR | 10-2020-0079427 | A | 7/2020 |
| KR | 10-2020-0135052 | A | 12/2020 |
| KR | 20200135052 | | 12/2020 |

OTHER PUBLICATIONS

International Search Report for International Application No. PCT/KR2021/019385 (ISA/KR) mailed Mar. 31, 2022 (2 pages).

Written Opinion for International Application No. PCT/KR2021/019385 (ISA/KR) mailed Mar. 31, 2022 (4 pages).

Extended European Search Report for EP Patent Application No. 21933391.1 dated Feb. 5, 2025 (10 pages).

Zhao, Pengfei et al., "*Strain-Discriminable Pressure/Proximity Sensing of Transparent Stretchable Electronic Skin Based on PEDOT:PSS/SWCNT Electrodes*", Applied Materials & Interfaces, [online] vol. 12, No. 49, Dec. 9, 2020, pp. 55083-55093.

Ozioko, Oliver et al., "*Carbon Nanotube/PEDOT: PSS Composite-based Flexible Temperature Sensor with Enhanced Response and Recovery Time*", 2020 IEEE International Conference on Flexible and Printable Sensors and Systems (FLEPS), IEEE, Aug. 16, 2020, pp. 1-4.

* cited by examiner

WEARABLE PRESSURE ULCER DETECTION SENSOR AND PRESSURE ULCER DETECTION SYSTEM INCLUDING THE SAME

TECHNICAL FIELD

The present invention relates to a wearable pressure ulcer detection sensor and a pressure ulcer detection system including the same, and more particularly, to a wearable pressure ulcer detection sensor and detection system that may be attached to a subject at risk of developing pressure ulcers and may measure the risk of the pressure ulcers in real time, thereby preventing pressure ulcers in advance.

BACKGROUND ART

A pressure ulcer is an ischemic skin ulcer that occurs when pressure is continuously applied to one part of the body, causing blood circulation problems in that area, which results in the lack of oxygen and nutrient supply. Although a pressure ulcer is a familiar disease, the severity thereof has been largely overlooked for a long time. This disease is divided into four stages. In a first stage, it is difficult for doctors to visually identify abnormal symptoms or for patients to feel them, and in this case, if a treatment period is missed and the disease progresses to a second stage or higher, extensive skin and bone transplant surgery is required, and it is a serious disease with a high risk of death from infectious diseases, such as sepsis, even after surgery. Current pressure ulcer prevention methods mainly rely on the labor of nursing staff to continuously change the patient's position, making it difficult to prevent the disease, and once pressure ulcer develops, the pressure ulcer progresses very quickly, resulting in increased physical and mental pain for patients and their guardians and a rapid rise in medical costs. Therefore, pressure ulcers urgently need the development of a prevention system and treatment.

Recently, technology using the Internet of Things (IoT) has developed rapidly, but it remains at the level of collecting a pressure distribution of a mat equipped with an elastic film using a pressure sensor or reporting the risk of pressure ulcers based on the time when the patient's movement stops.

Accordingly, there is a need for the development of an early detection system that may monitor the status of a risk area (or a pressure ulcer lesion area) in real time in an initial state where pressure ulcers are difficult to identify with the naked eyes or in abnormal conditions that may progress to pressure ulcers, detect the risk of developing pressure ulcers or the degree of progression of pressure ulcers in real time, and transfer detection results to patients, caregivers, guardians, and doctors in real time.

RELATED ART DOCUMENT

Patent Document

Korean Application Publication No. 2020-0135052
Korean Application Publication No. 2020-0048938

DISCLOSURE

Technical Problem

An object of the present invention is to provide a pressure ulcer sensor capable of bidirectional sensing that may simultaneously measure external stimuli and internal (skin tissue) changes.

Another object of the present invention is to provide a pressure ulcer sensor capable of monitoring a condition of areas suspected of developing pressure ulcers in real time and providing a discrimination index enabling early diagnosis of pressure ulcers.

Another object of the present invention is to provide a pressure ulcer sensor that may be simply attached to an area suspected of developing pressure ulcers to sense a magnitude of external stimuli causing pressure ulcers and changes in biometric signals due to damage to skin tissues.

Another object of the present invention is to provide a pressure ulcer detection system that may monitor the risk of developing pressure ulcers or a condition of areas suspected of developing pressure ulcers in real time from a distance.

Technical Solution

A wearable pressure ulcer detection sensor according to the present invention includes a pressure sensor measuring pressure based on a change in capacitance caused by physical force, a temperature sensor measuring temperature based on a change in electrical conductivity due to electron hopping, and an impedance sensor including two electrodes spaced apart from each other and in contact with skin.

In the wearable pressure ulcer detection sensor according to an exemplary embodiment of the present invention, the pressure sensor may include a polymer gel electrolyte capacitor.

In the wearable pressure ulcer detection sensor according to an exemplary embodiment of the present invention, the temperature sensor may include a conductive polymer matrix and a carbon nanostructure dispersed and embedded in the matrix.

In the wearable pressure ulcer detection sensor according to an exemplary embodiment of the present invention, the carbon nanostructure may include carbon nanotubes, graphene, or a mixture thereof.

In the wearable pressure ulcer detection sensor according to an exemplary embodiment of the present invention, the two electrodes of the impedance sensor may each be a composite of an insulating elastomer and a conductive nanowire.

In the wearable pressure ulcer detection sensor according to an exemplary embodiment of the present invention, the pressure ulcer detection sensor may further include a fabric substrate with a wiring formed on one surface thereof, and the pressure sensor, the temperature sensor, and the impedance sensor are arranged to be spaced apart from each other on one surface of the fabric substrate.

In the wearable pressure ulcer detection sensor according to an exemplary embodiment of the present invention, the pressure ulcer detection sensor may further include a wettable polymer foam covering the one surface of the fabric substrate, and the wettable polymer foam includes a through-hole formed so that the pressure sensor, the temperature sensor, and the impedance sensor are exposed to the surface.

The present invention includes a wearable pressure ulcer detection system including the wearable pressure ulcer detection sensor described above.

The wearable pressure ulcer detection system according to the present invention includes: a wearable pressure ulcer detection sensor described above, a microprocessing unit electrically connected to the pressure ulcer detection sensor, receiving sensing values from the pressure sensor, the temperature sensor, and the impedance sensor of the pressure ulcer detection sensor, and calculating a pressure ulcer indicator including pressure applied to a user's body to which the pressure ulcer detection sensor is attached, a skin temperature value, and a tissue impedance value, and a wireless communication unit transmitting the pressure ulcer indicator calculated by the microprocessing unit to a terminal device through wireless communication.

In the wearable pressure ulcer detection system according to an exemplary embodiment of the present invention, the microprocessing unit and the wireless communication unit may be provided on a flexible printed circuit board (PCB).

In the wearable pressure ulcer detection system according to an exemplary embodiment of the present invention, the wireless communication may include short-range wireless communication including WIFI or Bluetooth.

Advantageous Effects

The pressure ulcer detection system according to the present invention has the advantage of being able to detect in advance whether pressure ulcers have occurred or the risk of developing pressure ulcers at a time when it is difficult to determine the occurrence of pressure ulcers with the naked eyes by providing a skin temperature of an area suspected of developing pressure ulcers and impedance of the internal tissue, as well as pressure applied to the area suspected of developing pressure ulcers, using a pressure sensor, a temperature sensor, and an impedance sensor with wearable characteristics.

BEST MODE

Figure 1:
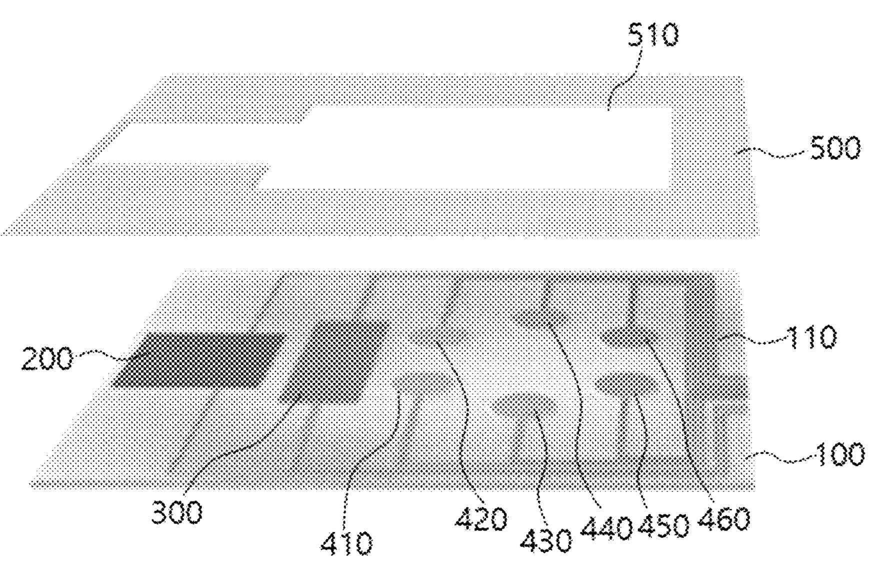
FIG. 1 is a diagram illustrating a configuration of a pressure ulcer detection sensor according to an exemplary embodiment of the present invention.
Figure 2:
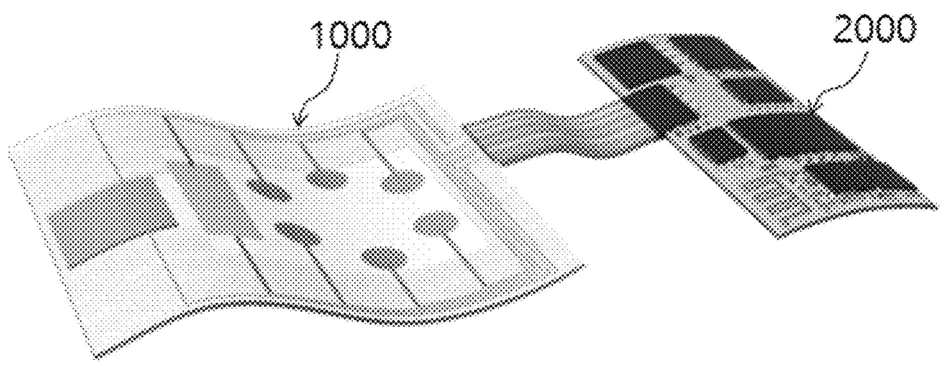
FIG. 2 is a diagram illustrating a configuration of a pressure ulcer detection system according to an exemplary embodiment of the present invention.

Hereinafter, a wearable pressure ulcer detection sensor according to the present invention will be described in detail with reference to the accompanying drawings. The drawings presented hereinafter are provided as examples to sufficiently transmit the technical concept of the present invention. Thus, the present invention is not limited to the drawings presented hereinafter and may be embodied in a different form, and the drawings present hereinafter may be exaggerated to be illustrated to clarify the technical concept of the present invention. Here, technical terms and scientific terms have the same meaning as generally understood by a person skilled in the art to which the present invention pertains, unless otherwise defined, and a detailed description for a related known function or configuration considered to unnecessarily divert the gist of the present invention will be omitted in the following descriptions and accompanying drawings.

Also, as used herein, the singular forms used in the specification and claims are intended to include the plural forms as well, unless the context clearly indicates otherwise.

In the following exemplary embodiments, terms, such as first, second, etc. are used for the purpose of distinguishing one component from another, not in a limiting sense.

In addition, terms, such as "including" or "having" means that the features or components described in the specification are present, and do not preclude the possibility that one or more other features or components will be added.

In this specification and the appended claims, when a portion of a film (layer), region, component, etc. is said to be on another portion, it is not only the case where the portion is directly on top of the other portion in contact therewith, but also the case where the portion is in contact with the other portion with another film (layer), other regions, and other components interposed therebetween.

A wearable pressure ulcer detection sensor according to the present invention includes a pressure sensor measuring pressure based on a change in capacitance caused by physical force; a temperature sensor measuring temperature based on a change in electrical conductivity due to electron hopping; and an impedance sensor including two electrodes spaced apart from each other and in contact with skin.

The wearable pressure ulcer detection sensor according to the present invention includes a pressure sensor, a temperature sensor, and an impedance sensor, so that the wearable pressure ulcer detection sensor according to the present invention is advantageously a two-way sensor capable of simultaneous detection of changes in biometric signals including temperature and impedance that change due to damage (abnormality) to skin tissues, as well as external stimuli including external pressure applied to the skin, that is, capable of simultaneous detection of changes in external stimuli and internal changes in the body.

In addition, the wearable pressure ulcer detection sensor according to the present invention provides an indicator for determining the degree of damage (abnormality) to skin tissue by detecting changes in temperature and impedance of an area (a skin area) suspected of developing pressure ulcers, and senses and provides pressure applied to the area suspected of developing pressure ulcers, so that a user (a user of the pressure ulcer detection sensor), a guardian, or medical staff may recognize and determine a level of risk of developing pressure ulcers before the pressure ulcer occurs. In addition, even if the user has already developed a pressure ulcer, the user, guardian, or medical staff may recognize and determine the degree of lesion progression (treatment) and speed of progression (treatment) at the area in which the pressure ulcer occurred.

In addition, in the wearable pressure ulcer detection sensor according to the present invention, as the pressure sensor calculates pressure based on a change in capacitance due to physical force (externally applied pressure), pressure may be measured in the form of an extremely thin film, securing wearable characteristics, and since pressure at the level occurring by the weight of the human body in a lying state may be precisely measured, the wearable pressure ulcer detection sensor according to the present invention is very advantageous for detecting a pressure ulcer.

The temperature sensor also measures temperature based on a change in electrical conductivity due to electron hopping, making it possible to measure temperature in the form of an extremely thin film, thereby securing wearable characteristics, and the impedance sensor measures impedance of skin tissue through two electrodes located to be spaced apart from each other and in contact with the user's skin, thereby securing wearable characteristics through electrodes that may be thinned.

In an advantageous example, the pressure sensor may include a polymer gel electrolyte capacitor. The polymer gel electrolyte capacitor may include a first electrode in contact with the user's skin; a polymer gel electrolyte; and a second electrode facing the first electrode with the polymer gel electrolyte interposed therebetween. As is known, the electrolyte of a thin film capacitor uses a liquid electrolyte, an inorganic electrolyte, or a polymer-based solid electrolyte. Liquid electrolyte-based capacitors are difficult to integrate into pressure ulcer sensors, have poor stability during use, and are not suitable due to poor inorganic electrolyte-based flexible characteristics. In thin film capacitors, polymer-based solid electrolytes may be broadly divided into solid polymer electrolytes, gel-type polymer electrolytes, and polyelectrolytes. Among them, gel-type polymer electrolytes are free from leakage and may achieve the highest ionic conductivity among solid electrolytes, but have the disadvantage of weak mechanical properties.

The pressure ulcer detection sensor according to an advantageous example of the present invention takes advantage of the disadvantages of such gel-type polymer electrolyte-based capacitors, and in detail, the pressure ulcer detection sensor according to an advantageous example of the present invention may measure pressure applied to an area suspected of developing pressure ulcers by using capacitance changing as ions are released from an ion pump inside the electrolyte by pressure caused by the weight of the human body, while securing flexible characteristics by the gel-type polymer electrolyte.

When pressure sensing is performed using a polymer gel electrolyte capacitor, a pressure sensor having high sensitivity having a wide pressure range including a pressure range of 4 to 13 kPa (30 to 100 mmHg), which is known to be applied to the skin when lying down in bed by adjusting the elastic modulus of the polymer gel electrolyte (gel type polymer electrolyte). As a practical example, the elastic modulus (the elastic modulus based on room temperature) of the polymer gel electrolyte of the polymer gel electrolyte capacitor may be very low at 0.01 to 1.00 kPa so that capacitance may be sensitively changed depending on the pressure in the pressure range of 4 to 13 kPa.

As known, polymer gel electrolytes may be acidic electrolytes or basic electrolytes and include polymers, such as poly(ethylene oxide) (PEO), poly(acrylate) (PA), poly(vinyl alcohol) (PVA), and poly(acrylic acid) (PAA), salts, such as potassium hydroxide, sulfuric acid, phosphoric acid, perchloric acid, etc., and solvents, such as water, and the elastic modulus of the polymer gel electrolyte may be appropriately adjusted by changing the content or specific material of the electrolyte components.

The two electrodes (first electrode and second electrode) of the polymer gel electrolyte capacitor may be electrodes commonly used in solid capacitors and may include for example, transparent conductive oxide, such as indium tin oxide, nanowire network, such as silver nanowire, etc., conductive two-dimensional carbon structures, such as graphene, conductive one-dimensional carbon structures, such as carbon nanotubes, and conductive polymers, such as activated carbon, (poly(3,4-ethylenedioxythiophene):poly (styrenesulfonate) (PEDOT:PSS), but are not limited thereto. In addition, specific dimensions of the polymer gel electrolyte capacitor may be sufficient to smoothly measure the pressure applied to the area suspected of developing pressure ulcers. Practical examples may include a width of 1 mm to 5 cm, a breadth of 1 mm to 5 cm, and a thickness of the polymer gel electrolyte at the level of 10 to 100 μm but are not limited thereto.

The temperature sensor may monitor changes in body temperature in areas suspected of developing pressure ulcers due to skin tissue abnormalities or inflammation. In an advantageous example, the temperature sensor may include a conductive polymer matrix and carbon nanostructures dispersed and embedded in the matrix. Substantially, the temperature sensor may include a thin film of a composite including a conductive polymer matrix and carbon nanospheres dispersed and embedded in the conductive polymer matrix.

The conductive polymer of the conductive polymer matrix may be one or two or more selected from the group consisting of polyacetylene-based, polyaniline-based, polypyrrole-based, and polythiophene-based conductive polymers, but is not limited thereto. As a practical example, conductive polymers may be any one or two or more selected from polyacetylene (PA), polyaniline (PANI), polypyrrol PPy, polythiophen (PT), poly(3,4-ethylenedioxythiophene (PEDOT), polyisothianaphthene (PITN), polyphenylene vinylene (PPV), polyphenylene (PPE), polyphenylene sulfide (PPS), polysulfur nitride (PSN), etc.

The carbon nanostructure may be a conductive carbon nanostructure, and the conductive carbon nanostructure may include, but is not limited to, carbon nanotubes, graphene (including reduced graphene oxide (RGO)), or mixtures thereof.

In the aforementioned composite thin film (a composite thin film), charge transfer is made by electron hopping at an interface of the composite, and as the temperature increases, the amount of electrons at the interface increases and resistance decreases. Accordingly, by measuring the electrical properties of the thin film of the composite, the temperature of the area suspected of developing pressure ulcers may be sensed. At this time, of course, the electrical characteristics may include electrical conductivity or electrical resistance.

Considering a normal temperature of the human body and a variable abnormal body temperature, a temperature in the range of 35 to 45° C. may be an effective temperature range that may be accurately detected by a temperature sensor. The sensing sensitivity of the temperature sensor for this effective temperature range may be secured by adjusting the range of an interface (an interface area) between the conductive polymer and the carbon nanostructure in the composite.

In order for the electrical properties of the composite thin film to change sensitively according to temperature changes in the effective temperature range, the composite thin film may include carbon nanotubes as a carbon nanostructure, and a weight ratio of conductive polymer matrix:carbon nanotubes may be 1:0.3 to 0.5. However, temperature sensing is not impossible outside this range, and thus, the present invention is not limited by a specific composition or material of the composite thin film.

The specific dimension of the composite thin film may be sufficient to smoothly measure the temperature of the area suspected of developing pressure ulcers. As a practical example, the specific dimensions of the composite thin film has a width of 0.5 mm to 2.0 mm, a breadth of 0.5 mm to 1.0 mm, and a thickness of 100 to 300 μm, etc., but is not limited thereto.

The impedance sensor may include two electrodes spaced apart from each other, and each of the two electrodes may be a composite of an insulating elastomer and a conductive nanowire. Specifically, the two electrodes may each be a composite including a substrate of an insulating elastomer and conductive nanowires that are dispersed and bonded to the substrate of the insulating elastomer to form a network.

At this time, a network of conductive nanowires may refer to a structure in which a continuous current movement path is formed by bonding or contact between conductive nanowires. The insulating elastomer may be a curable resin having high flexibility and elasticity, and may include, but are not limited to, for example, siloxane-based resin, olefin-based elastic resin, or polyurethane-based resin. The conductive nanowire may be a metal nanowire, and the metal nanowire may include nanowires of silver, gold, copper, nickel, or mixtures thereof, or core-shell nanowires thereof, but is not limited thereto.

The related art hydrogel-based electrodes are difficult to use for a long period of time due to moisture easily evaporating and reduced adhesion due to contamination of the electrode surface and have insufficient flexibility or elasticity, so they have limitations as wearable sensors that should be attached for a long period of time. Meanwhile, the electrode of the impedance sensor according to an exemplary embodiment, which is based on a composite of an insulating elastomer and a conductive nanowire, may secure excellent flexible characteristics and may adhere stably and steadily to areas suspected of developing pressure ulcers due to the weight of a lying human body, and stable contact between the metal nanowire and the skin may be maintained for a long period of time.

The specific dimensions of each of the two electrodes of the impedance sensor may be sufficient to smoothly measure the impedance of the skin tissue in the area suspected of developing pressure ulcers. For example, the width and breadth of the electrodes may each be 1 mm to 1 cm, and a distance between the two electrodes may be 0.5 cm to 5 cm, but are not limited thereto.

The impedance of skin tissue may be at the level of several MΩ for healthy skin and at the level of tens of kΩ for damaged skin, and as damage is severe, the impedance is lower. Accordingly, by measuring the impedance of the skin tissue using an impedance sensor, whether the skin tissue is damaged or the degree of damage in the area suspected of developing pressure ulcers may be detected. At this time, an alternating current (AC) frequency range applied to the two electrodes to measure the impedance may be at the level of $10^0$ to $10^6$ Hz, and the magnitude of the AC voltage may be at the level of several mV, specifically, at the level of 2 to 10 mV, and the AC may have the form of a sine wave, but is not limited thereto.

Furthermore, the impedance of the area suspected of developing pressure ulcers (skin tissue) may be measured by AC voltage applied to the two electrodes of the impedance sensor, and at the same time, fine electrical stimulation may be applied to the area suspected of developing pressure ulcers.

The pressure ulcer detection sensor according to an exemplary embodiment may further include a fabric substrate having a wiring formed on one surface thereof. The fabric substrate having the wiring may serve as a platform in which the pressure sensor, temperature sensor, and impedance sensor described above are integrated.

In addition, the pressure ulcer detection sensor according to an exemplary embodiment may further include a wettable polymer foam that covers one surface of the fabric substrate, and the wettable polymer foam may include a through-hole formed so that the pressure sensor, temperature sensor, and impedance sensor are exposed to the surface therethrough.

FIG. 1 is an example of a configuration diagram of a pressure ulcer detection sensor according to an exemplary embodiment of the present invention.

As an example shown in FIG. 1, the pressure ulcer detection sensor may include a fabric substrate 100 on which a wiring 110 is formed, a pressure sensor 200, a temperature sensor 300, impedance sensors 410 to 460, and a wettable polymer foam 500 having a through-hole 510. The fabric substrate 100 has flexible characteristics and conformal characteristics that protect the sensor from moisture, dust, chemicals, etc., and may provide a platform having excellent ventilation. The fabric substrate 100 may be provided with the wiring 110 formed using conductive ink, etc., and each of the pressure sensor 200, the temperature sensor 300, and the impedance sensors 410 to 460 may be electrically connected to the outside of the fabric substrate 100.

The wettable polymer foam 500 may absorb sweat or body fluids, so the sensitivity of each integrated sensor (the pressure sensor 200, the temperature sensor 300, and the impedance sensors 410 to 460) may be maintained stably. The wettable polymer foam 500 may include moisture and may include a biosafety material. As an example, the wettable polymer foam may be a foam of hydrophilic polymers, such as polyvinyl alcohol, polyethylene glycol, polyethylene oxide, polyvinyl acrylic acid, polymethacrylic acid, polyurethane, or a foam of a mixture of hydrophilic polymers and a cellulose esters or cellulose ether materials, such as carboxymethyl cellulose, carboxymethyl hydroxyethyl cellulose, methyl cellulose, hydroxyethyl methylcellulose, hydroxypropyl methylcellulose, ethyl hydroxyethyl cellulose, hydroxyethyl cellulose, hydroxypropyl cellulose, and hydroxyethyl hydroxypropyl cellulose, but is not limited thereto.

The wettable polymer foam 500 may have a shape and size corresponding to the fabric substrate 100 and may include the through-hole 510 formed so that the pressure sensor 200, the temperature sensor 300, and the impedance sensors 410 to 460 integrated into the fabric substrate 100 are exposed to the surface. Accordingly, each of the sensors 200, 300, and 410 to 460 integrated into the fabric substrate 100 may be exposed through the through-hole in the wettable polymer foam 500 and directly contact the user's skin. Accordingly, when the pressure ulcer detection sensor is actually used, the wettable polymer foam 500 may be in contact with the human body and the fabric substrate 100 may be a layer covering the skin.

In addition, as an example shown in FIG. 1, the impedance sensor may have two or more monomers based on two electrodes (410 to 420, 430 to 440, or 450 to 460) to which a voltage transmitted through the wiring 110 formed on the fabric substrate 100 is applied as one monomer for impedance measurement. An example in FIG. 1 is an example provided with three monomers. If the impedance sensor includes two or more monomers, abnormalities in skin tissue may be effectively detected even in areas suspected of developing pressure ulcers. Of course, the number of provided monomers, the location of each monomer, and a distance between the two electrodes in each monomer may be appropriately adjusted by taking into account the specific area and shape of the area suspected of developing pressure ulcers.

The present invention includes a wearable pressure ulcer detection system including the wearable pressure ulcer detection sensor described above.

The wearable pressure ulcer detection system according to the present invention may include the wearable pressure ulcer detection sensor described above; a microprocessing unit electrically connected to the pressure ulcer detection sensor, receiving sensing values from a pressure sensor, a temperature sensor, and an impedance sensor of the pressure ulcer detection sensor, and calculating a pressure ulcer indicator including pressure applied to the user's body to which the pressure ulcer detection sensor is attached, skin temperature value, and a tissue impedance value, and a wireless communication unit transmitting the pressure ulcer indicator calculated by the microprocessing unit to a terminal device through wireless communication.

Advantageously, the microprocessing unit and the wireless communication unit may be provided on a flexible printed circuit board (PCB) and may be electrically connected to the wearable pressure ulcer detection sensor described above.

The related art wearable sensors are generally connected to external devices through a wiring for data processing and transmission/reception. As a result, there are problems in that wearing comfort of the wearable sensor is reduced and mobility is limited.

However, in the wearable pressure ulcer detection system according to the present invention, the microprocessing unit for data processing and the wireless communication unit for wireless communication are integrated on the flexible PCB and connected to the pressure ulcer detection sensor 1000 through a flexible wiring, so that a flexible PCB 2000 in which the microprocessing unit and the wireless communication unit are integrated may be located near the human body (the user), thereby preventing foreign body sensation during use and not damaging mobility.

Figure 3:
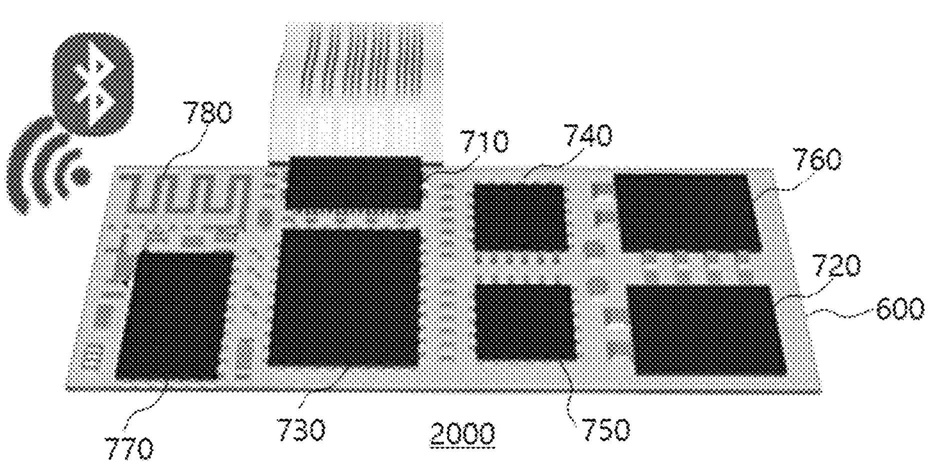
FIG. 3 is a diagram illustrating a configuration of a wireless communication unit and a microprocessing unit integrated in a flexible printed circuit board (PCB) in a pressure ulcer detection system according to an exemplary embodiment of the present invention.

FIG. 3 is an example of a configuration diagram of a flexible PCB in which a microprocessing unit and a wireless communication unit are integrated.

As an example shown in FIG. 3, the microprocessing unit may include a micro-impedance analyzer 740 detecting a change in impedance, a low-pass filter 720 performing signal filtering, and an AC chip 750 detecting a change in temperature and pressure, and outputs thereof may be converted into digital signals through a micro-controller 730. Power is supplied to the sensors through a connection portion 710, and sensed values are output. In detail, a temperature sensor detects a change in temperature according to a change in resistance of a composite thin film including a conductive polymer matrix and carbon nano structures dispersed and embedded in the matrix, and thus, the temperature sensor may perform control and measurement using a digital temperature sensor module controller, such as ON Semiconductor's NCT75 controller. A pressure sensor may detect pressure through a change in capacitance, and thus, the pressure sensor may perform control and measurement using a capacitive touch screen controller, such as MICROCHIP's CAP1203 controller. Finally, the measured signals may be transferred to the micro-controller 730 and a final signal may be calculated and converted into a digital signal.

Accordingly, the signals digitally output from the micro-controller 730 may include pressure applied to the area suspected of developing pressure ulcers, a skin temperature of the area suspected of developing pressure ulcers, and an internal skin tissue impedance value of the area suspected of developing pressure ulcers. The pressure applied to the body, the skin temperature, and the tissue impedance values may be transmitted to terminal devices of related persons, such as doctors and users of the pressure ulcer detection sensors, guardians, and the like through the wireless communication unit, as indicators (pressure ulcer indicators) that may medically determine the risk of developing pressure ulcers or the progress of pressure ulcers.

The wireless communication unit may include a transmitter 770 or a transceiver 770 and an antenna 780 that transmits or receives electromagnetic waves of a certain frequency. Wireless communication may be short-distance wireless communication, such as Bluetooth or Wi-Fi. In the case of low-power Bluetooth, wireless communication is possible over 10 m, and in the case of using a mesh Bluetooth method, hundreds of Bluetooth devices may be connected at once in one device, allowing pressure ulcer indicators to be transmitted to the terminal devices of various people involved.

At this time, when the wireless communication unit includes a transceiver, signals transmitted from terminal devices, such as doctors, pressure ulcer detection sensor users, and guardians may be received, and based on the received signals, ON/OFF of the pressure ulcer detection sensor, a transmission interval of pressure ulcer indicators, and selective transmission of only specific indicators among various pressure ulcer indicators may be controlled, and a power source that supplies power to the microprocessing unit, wireless communication unit, and pressure ulcer detection sensor, for example, a battery 760 may be provided on the flexible PCB 600.

Hereinabove, although the present invention is described by specific matters, exemplary embodiments, and drawings, they are provided only for assisting in the entire understanding of the present invention. Therefore, the present invention is not limited to the exemplary embodiments. Various modifications and changes may be made by those skilled in the art to which the present invention pertains from this description.

Therefore, the spirit of the present invention should not be limited to the aforementioned exemplary embodiments, and the following claims as well as all modified equally or equivalently to the claims are intended to fall within the scope and spirit of the invention.

The invention claimed is:

1. A wearable pressure ulcer detection sensor comprising:

a pressure sensor configured to measure pressure on a body of a user;

a temperature sensor configured to measure temperature on the body of the user;

an impedance sensor including two electrodes spaced apart from each other and configured to be in contact with skin of the user to measure tissue impedance;

a microprocessing unit electrically connected to the pressure ulcer detection sensor, wherein the microprocessing unit is configured to:

receive pressure values from the pressure sensor, temperature values from the temperature sensor, and tissue impedance values from the impedance sensor, and calculate a pressure ulcer indicator to determine a risk of developing pressure ulcers, the pressure ulcer indicator including a pressure, a temperature, and a tissue impedance value; and a wireless communication unit configured to transmit the pressure ulcer indicator to a terminal device including a doctor's device, a user's device, or a guardian's device, wherein based on a signal from the terminal device, the following are controlled by the microprocessing unit: ON/OFF of the pressure ulcer detection sensor, a transmission interval of the pressure ulcer indicator, and a selective transmission of only specific values among the pressure, the temperature, and the tissue impedance.

2. The wearable pressure ulcer detection sensor of claim 1, wherein the pressure sensor includes a polymer gel electrolyte capacitor.

3. The wearable pressure ulcer detection sensor of claim 1, wherein the temperature sensor includes a conductive polymer matrix and a carbon nanostructure dispersed and embedded in the matrix.

4. The wearable pressure ulcer detection sensor of claim 3, wherein the carbon nanostructure includes carbon nanotubes, graphene, or a mixture thereof.

5. The wearable pressure ulcer detection sensor of claim 1, wherein the two electrodes of the impedance sensor each are a composite of an insulating elastomer and a conductive nanowire.

6. The wearable pressure ulcer detection sensor of claim 1, wherein the pressure ulcer detection sensor further includes a fabric substrate with a wiring formed on one surface thereof, and the pressure sensor, the temperature sensor, and the impedance sensor are arranged to be spaced apart from each other on one surface of the fabric substrate.

7. The wearable pressure ulcer detection sensor of claim 6, wherein the pressure ulcer detection sensor further includes a wettable polymer foam covering the one surface of the fabric substrate, and the wettable polymer foam includes a through-hole formed so that the pressure sensor, the temperature sensor, and the impedance sensor are exposed to the one surface.

8. The wearable pressure ulcer detection sensor of claim 1, wherein the microprocessing unit and the wireless communication unit are provided on a flexible printed circuit board (PCB).

9. The wearable pressure ulcer detection sensor of claim 1, wherein the wireless communication unit is configured for short-range wireless communication.

* * * * *